United States Patent [19]

Balke et al.

[11] 4,014,879

[45] Mar. 29, 1977

[54] CONTINUOUS PROCESS FOR THE PRODUCTION OF 2-ALKYL OR CYCLOALKYL-4-METHYL-6-HYDROXY-PYRIMIDINES

[75] Inventors: David E. Balke; Donald E. Perez, both of Mobile, Ala.; Yel S. Sury, Greensboro, N.C.

[73] Assignee: Ciba-Geigy Corporation, Ardsley, N.Y.

[22] Filed: July 3, 1975

[21] Appl. No.: 593,100

[52] U.S. Cl. .................................. 260/251 R
[51] Int. Cl.² ............................. C07D 239/26
[58] Field of Search ........................ 260/251 R

[56] References Cited

OTHER PUBLICATIONS

Snyder, et al.: J. Am. Chem. Soc., vol. 76, p. 121 relied upon (1954).

Primary Examiner—Lewis Gotts
Assistant Examiner—Dolph H. Torrence
Attorney, Agent, or Firm—Karl F. Jorda

[57] ABSTRACT

Production of 2-alkyl or cycloalkyl-4-methyl-6-hydroxy-pyrimidines through a continuous ring closure/neutralization process which increases equipment capacity by a minimum of 45% and yield of about 10% over the usual batch process.

2 Claims, No Drawings

CONTINUOUS PROCESS FOR THE PRODUCTION OF 2-ALKYL OR CYCLOALKYL-4-METHYL-6-HYDROXY-PYRIMIDINES

The present invention relates to an improvement in the manufacturing process for 2-alkyl or 2-cycloalkyl-4-methyl-6-hydroxy-pyrimidines of the general formula

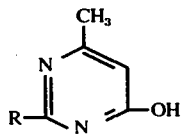
(I)

wherein R represents an alkyl or a cycloalkyl group.

Alkyl groups denoted by R are straight-chain or branched-chain groups having preferably 1 to 4 carbon atoms, such as, methyl, ethyl, n-propyl, isopropyl, n-butyl, secondary butyl, isobutyl or tertiary butyl.

Cycloalkyl groups denoted by R have 3 to 6 ring carbon atoms. Preferred cycloalkyl groups are cyclopropyl, cyclopentyl or cyclohexyl.

The compounds of formula I have particular importance as intermediates for, e.g., the preparation of active substances for pest control and are conventionally produced by a batch process. In the batch process, variables of temperature and pH which are critical to achieve high yields, are difficult to control.

The present invention aims at improvement of yields through a continuous process which increases equipment capacity by a minimum of 45% and yield of about 10% over the batch process, and produces oxypyrimidines of formula I of improved quality and at an overall yield of 90 to 92%.

For the process according to the invention, an amidine of the formula

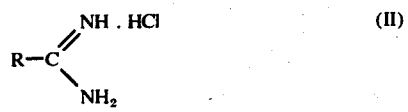
(II)

is fed continuously into a first-stage reactor simultaneously with an excess of methylacetoacetate and an aqueous alkali solution for pH control. After a retention time of 1 hour at a temperature of 40° to 45° C, preferably at 40° C, the reaction mass from the first stage is continuously fed to a second stage reactor simultaneously with another amount of aqueous alkali solution for pH control. Suitable alkalis are the hydroxides and carbonates of alkali metals, especially sodium hydroxide. After a further retention time of about 1.5 hours at a temperature of 40° to 45° C, preferably at 40° C, the resulting slurry of alkali-oxypyrimidine of the formula

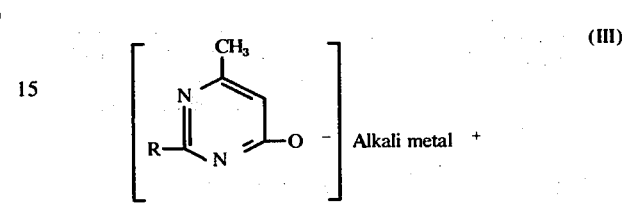
(III)

is continuously fed to the neutralizer with simultaneous addition of an inorganic or organic acid, preferably, by addition of hydrochloric acid.

In the formulae II and III, R has the same meaning as given for the formula I.

The two stages of the ring closure step are performed at a pH of about 12 to 12.5 and under normal pressure.

The continuous neutralization is performed at a pH between about 6 and 7, and a temperature range of about 0° to 10° C, preferably at 5° C and also under normal pressure. The residence time for the continuous neutralization step is about 60 minutes or less.

Compounds of the formula II are known and may be prepared by the following known continuous ethyliminoether hydrochloride and amidine hydrochloride processes:

a) Iminoether Step:

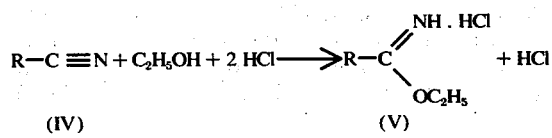

b) Amidine Step:

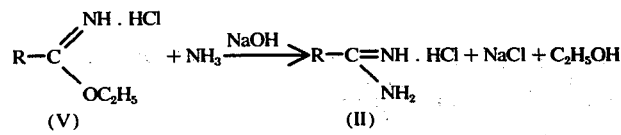

In the formulae II to V, R has the same meaning as given for formula I.

For a further understanding of the invention a representative and non-limitative example follows. It is provided merely for illustrative purposes. The temperatures are in degrees centigrade.

EXAMPLE

Preparation of 2-Isopropyl-4-methyl-6-hydroxy-pyrimidine

A. Preparation of Intermediates

Iminoether Step:

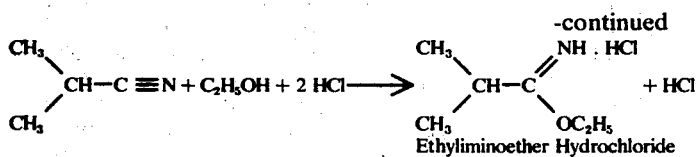

The ethyliminoether hydrochloride is produced in a three-stage reaction system, as follows:

Stage 1:
Isobutyronitrile, ethanol (7% mole excess) and anhydrous gaseous hydrochloric acid are simultaneously fed to the first stage maintained at 40° with a retention time of 1 hour. The hydrochloric acid level should be between 18 to 19%.

Stage 2 and 3:
The partially converted reaction mass from Stage 1 is fed to Stage 2 and then to Stage 3. Both stages should be maintained at 25° with retention times of 3 hours in each. The hydrochloric acid level should be maintained at 20 to 22% by sufficient addition of HCl to Stage 2. A 95 to 97% conversion of isobutyronitrile to the ethyliminoether hydrochloride is obtained from the three stages of Step 1.

Amidine Step:

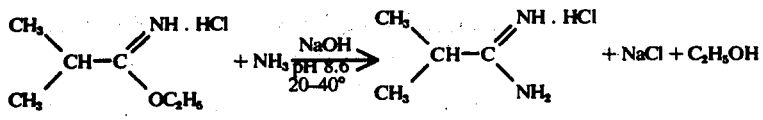

The conversion of the ethyliminoether to the isobutyroamidine hydrochloride (amidine) is accomplished in a one-stage reactor. The iminoether from the previous step and 29% aqueous ammonia (20 to 30% aqueous ammonia or anhydrous ammonia can be used) is continuously fed into the single-stage reactor. The reactor conditions are as follows:

| | |
|---|---|
| Temperature | 20 to 40° |
| pH | 8.6 |
| Retention time | 2 to 2.5 hours and 10% ammonia excess |

A 96 to 98% conversion of the ethyliminoether to the amidine is obtained.

B. Continuous Ring-closure and Neutralization Step:
Ring-closure Step:

Ring-closure Step:

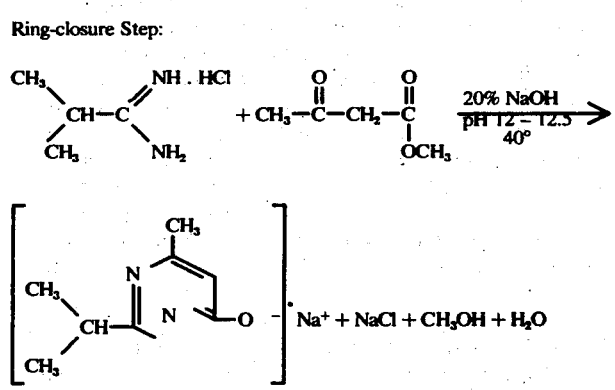

The conversion of isobutyroamidine hydrochloride to oxypyrimidine sodium salt is accomplished in a two-stage reactor. The amidine from step 2 is fed continuously into the first-stage reactor simultaneously with methylacetoacetate and the aqueous 50% NaOH solution for pH control. The reactor conditions are as follows: temperature 40 to 45°, pH 12.5, retention time one hour and 20 to 30% methylacetoacetate excess. For the second stage the reaction mass from the first stage is then continuously fed to the second-stage reactor simultaneously with the aqueous 50% NaOH solution for pH control.

The temperature is controlled in the ring-closure reactors with a warm (40° to 45°) water bath circulating through the reactor jackets.

A 98 to 100% conversion of isobutyroamidine hydrochloride to the oxypyrimidine sodium salt is obtained.

Neutralization Step:

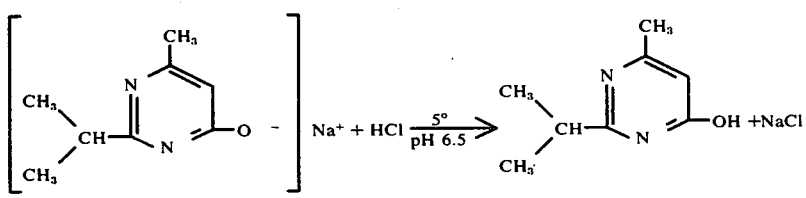 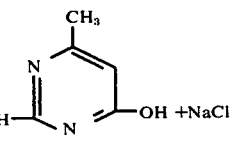

The oxypyrimidine sodium salt slurry is continuously fed to the neutralizer with simultaneous addition of 32% HCl. The neutralizer conditions are as follows: temperature 5°, pH 6.5, residence time 30 minutes.

The neutralizer temperature is controlled with a constant temperature water bath. The pH is monitored by electrode and pH paper.

The precipitated crystals of 2-isopropyl-4-methyl-6-hydroxypyrimidine are filtered off, thoroughly washed with water and dried.

The conversion to 2-isopropyl-4-methyl-6-hydroxypyrimidine in the form of white crystals is 100%.

Overall, the conversion of isobutyronitrile to the oxypyrimidine according to the present continuous process is 90 to 92%, compared to yields from conventional batch processes of 83 to 84%.

If in the above process, cyclopropanecarbonitrile is substituted for isobutyronitrile, 2-cyclopropyl-4-methyl-6-hydroxypyrimidine is obtained in an analogous manner at an over all yield of 90%.

What is claimed is:

1. A continuous ring-closure/neutralization process for the preparation of a 2-alkyl or 2-cycloalkyl-4-methyl-6-hydroxy-pyrimidine of the formula

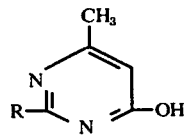

wherein R represents alkyl of 1 to 4 carbon atoms and cycloalkyl of 3 to 6 carbon atoms, which process comprises 1. a continuous ring-closure step in two stages wherein:
  a. an amidine of the formula

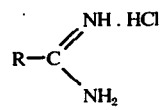

wherein R has the same meaning as given above, is fed continuously into a first-stage reactor simultaneously with methylacetoacetate and an aqueous alkali solution for pH control, for a retention time of about one hour at a temperature of 40° to 45° C, and
  b. the reaction mass is then continuously fed to a second-stage reactor simultaneous with another amount of an aqueous alkali solution for pH control for a further retention time of about one and a half hours at a temperature of 40° to 45° C, and
2. a continuous neutralization step wherein the resulting slurry of alkali oxypyrimidine of the formula

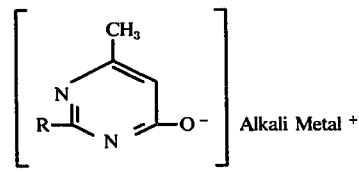

wherein R has the same meaning as given above, is continuously fed with simultaneous addition of an inorganic or organic acid to the neutralizer, wherein the continuous neutralization is performed at a pH between about 6 and 7, at a temperature ranging between about 0° to 10° C and a retention time of about 30 minutes.

2. A continuous process according to claim 1 for the preparation of 2-isopropyl-4-methyl-6-hydroxy-pyrimidine wherein the amidine is isobutyroamidine and the first ring-closure stage is performed with a 20 to 30% methylacetoacetate excess, at a pH of about 12 to 12.5, controlled with an aqueous 50% sodium hydroxide solution and at a temperature of about 40° C, the second ring-closure stage is carried out at a pH of about 12 to 12.5, controlled with a further amount of an aqueous 50% sodium hydroxide solution and at a temperature of about 40° C and the neutralization stage is performed at a pH of about 6.5, controlled by the simultaneous addition of 32% HCl, and at a temperature of about 5° C.

* * * * *

UNITED STATES PATENT OFFICE
CERTIFICATE OF CORRECTION

Patent No. 4,014,879                    Dated   March 29, 1977

Inventor(s) David E. Balke, et al

It is certified that error appears in the above-identified patent and that said Letters Patent are hereby corrected as shown below:

1) Column 2, b) Amidine Step, that portion of the formula,

"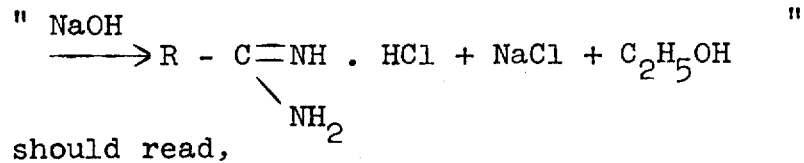"

should read,

-- 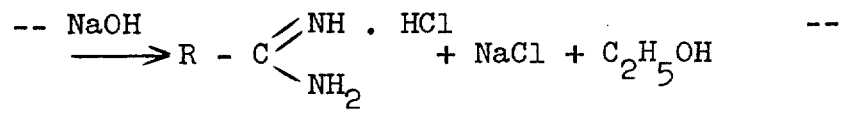 --

UNITED STATES PATENT OFFICE
CERTIFICATE OF CORRECTION

Patent No. 4,014,879     Dated March 29, 1977

Inventor(s) David E. Balke, et al

It is certified that error appears in the above-identified patent and that said Letters Patent are hereby corrected as shown below:

2) Column 4, in the formula, "

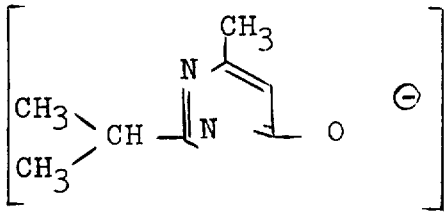

should read,

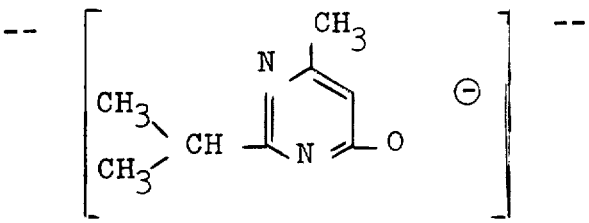

Signed and Sealed this

Twentieth Day of September 1977

[SEAL]

Attest:

RUTH C. MASON  
*Attesting Officer*

LUTRELLE F. PARKER  
*Acting Commissioner of Patents and Trademarks*